US00PP35128P2

(12) United States Plant Patent
Rietberg

(10) Patent No.: US PP35,128 P2
(45) Date of Patent: Apr. 25, 2023

(54) ***HEBE* PLANT NAMED 'HM1803011'**

(50) Latin Name: ***Hebe* hybrid**
Varietal Denomination: HM1803011

(71) Applicant: Henrik Christiaan Cozijn Rietberg, Wezep (NL)

(72) Inventor: Henrik Christiaan Cozijn Rietberg, Wezep (NL)

(73) Assignee: EDEN'S CREATIONS B.V., Wezep (NL)

( * ) Notice: Subject to any disclaimer, the term of this patent is extended or adjusted under 35 U.S.C. 154(b) by 0 days.

(21) Appl. No.: 17/744,178

(22) Filed: May 13, 2022

(51) Int. Cl.
*A01H 5/02* (2018.01)
*A01H 6/68* (2018.01)

(52) U.S. Cl.
USPC ..... Plt./251
CPC ..... *A01H 6/68* (2018.05)

(58) Field of Classification Search
USPC ..... Plt./251
CPC ..... A01H 6/68; A01H 5/68
See application file for complete search history.

(56) References Cited

PUBLICATIONS

The website, "All Blooms *Hebe*", downloaded from url: https://www.all-blooms.com/?lang=en, Mar. 8, 2021, downloaded on Sep. 1, 2022.*

* cited by examiner

*Primary Examiner* — Anne Marie Grunberg
(74) *Attorney, Agent, or Firm* — Penny J Aguirre

(57) ABSTRACT

A new cultivar of *Hebe* plant named 'HM1803011' that is characterized by its consistently healthy plants that have a low susceptibility to leaf spot disease and downy mildew, its compact plant habit, its leaves that are small in size, its flowers that are self-cleaning, and its flowers that are purple-pink in color.

2 Drawing Sheets

Botanical classification: *Hebe* hybrid.
Cultivar designation: 'HM1803011'.

CROSS REFERENCE TO A RELATED APPLICATION

This application is related to a European plant breeders' rights application filed on Sep. 15, 2020, application No. 2020/2159. The Applicant received the information for the Plant breeders' rights application directly from the Inventor.

BACKGROUND OF THE INVENTION

The present invention relates to a new and distinct cultivar of *Hebe*, botanically of hybrid origin, known as *Hebe* 'HM1803011', and will be referred to hereafter by its cultivar name, 'HM1803011'. 'HM1803011' is an evergreen shrub grown for use as a container plant and as a landscape shrub.

The new cultivar was derived from a controlled breeding program conducted by the Inventor in Wezep, The Netherlands. The goal of the breeding program is to select new cultivars of *Hebe* with improved plant health, compact plant habits, small leaves, abundant flowering, and self-cleaning flowers. The new cultivar arose from a cross made in September of 2017 between an unnamed and unpatented proprietary plants from the Inventor's breeding program; reference no. HM17-305 as the female parent and ref no. PM17-303 as the male parent. The Inventor selected 'HM1803011' in September of 2018 as a single unique plant amongst the seedlings that resulted from the above cross.

Asexual propagation of the new cultivar was first accomplished by stem cuttings in September 2018 by the Inventor in Wezep, The Netherlands. Asexual propagation by stem cuttings and tissue culture using meristematic tissue has determined the characteristics of the new cultivar are stable and reproduced true to type in successive generations.

SUMMARY OF THE INVENTION

The following traits have been repeatedly observed and represent the characteristics of the new cultivar, which in combination distinguish 'HM1803011' as a new and distinct cultivar of *Hebe*.

1. 'HM1803011' exhibits consistently healthy plants that have a low susceptibility to leaf spot disease and downy mildew.
2. 'HM1803011' exhibits a compact plant habit.
3. 'HM1803011' exhibits leaves that are small in size.
4. 'HM1803011' exhibits flowers that are self-cleaning.
5. 'HM1803011' exhibits flowers that are purple-pink in color.

The female parent of 'HM1803011' differs from 'HM1803011' in having a less compact plant habit, more susceptibility to leaf spot disease and downy mildew, flowers that are less intense in color, and a shorter flowering period. The male parent of 'HM1803011' differs from 'HM1803011' in having more susceptibility to leaf spot disease and downy mildew, flowers that are less intense in color, and a longer flowering period. 'HM1803011' can be most closely compared to the cultivars 'Rosie' and 'Branpink' (both un-patented). 'Rosie' is similar to 'HM1803011' in having self-cleaning flowers and floriferous blooming habit. 'Rosie' differs from 'HM1803011' in having more susceptibility to leaf spot disease and downy mildew, leaves that are longer and less round in shape, flowers that fade in color after opening, and flowers that are considerably less self-cleaning. 'Branpink' is similar to 'HM1803011' in having a compact plant habit and in leaf size. 'Branpink' differs from 'HM1803011' in having leaves that are slightly brown-green in color, inflorescences that are longer (more stretched) and pointed in shape, and flowers that are darker purple-pink in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by All-Blooms and floraxchange.

BRIEF DESCRIPTION OF THE DRAWINGS

The accompanying color photographs illustrate the overall appearance and distinct characteristics of the new *Hebe*. The photographs were taken of a 7-month-old plant of 'FSK17S28' as grown outdoors in a 12-cm container in Wezep, The Netherlands.

The photograph in FIG. 1 is a side view of 'HM1803011' in bloom.

Figure 1:
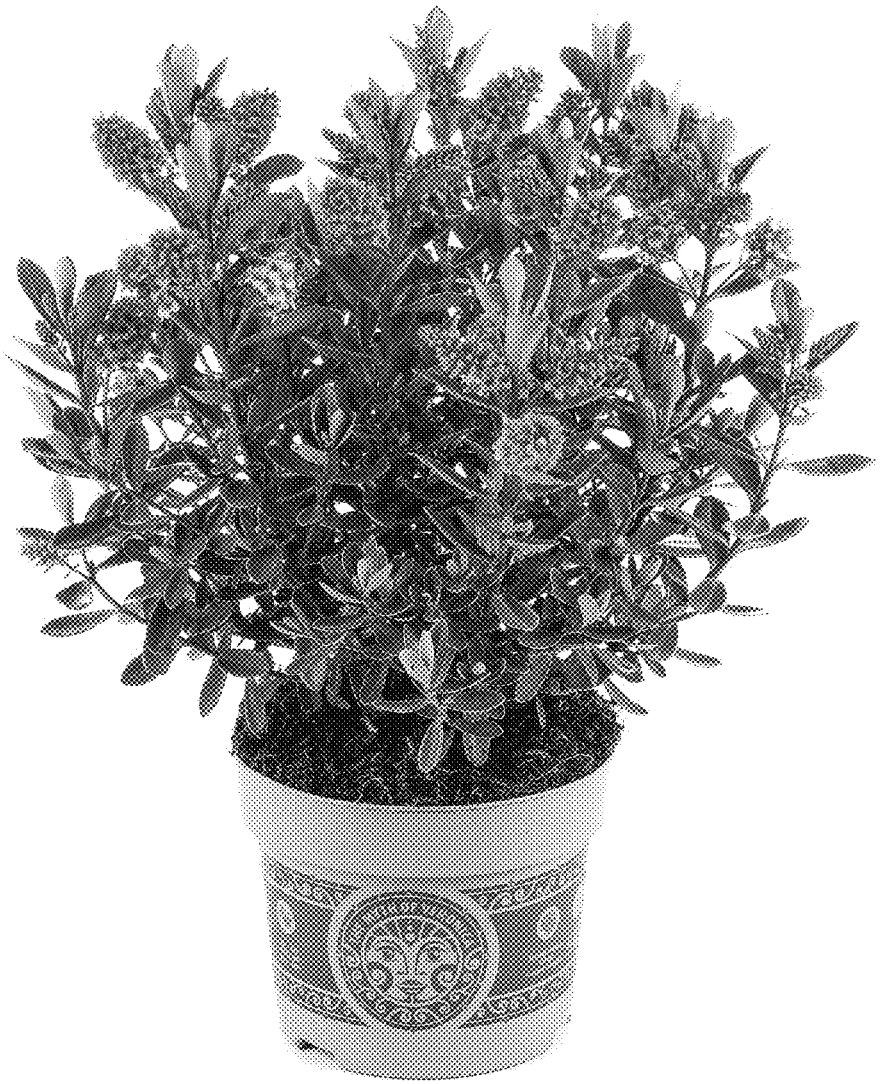
Figure 2:
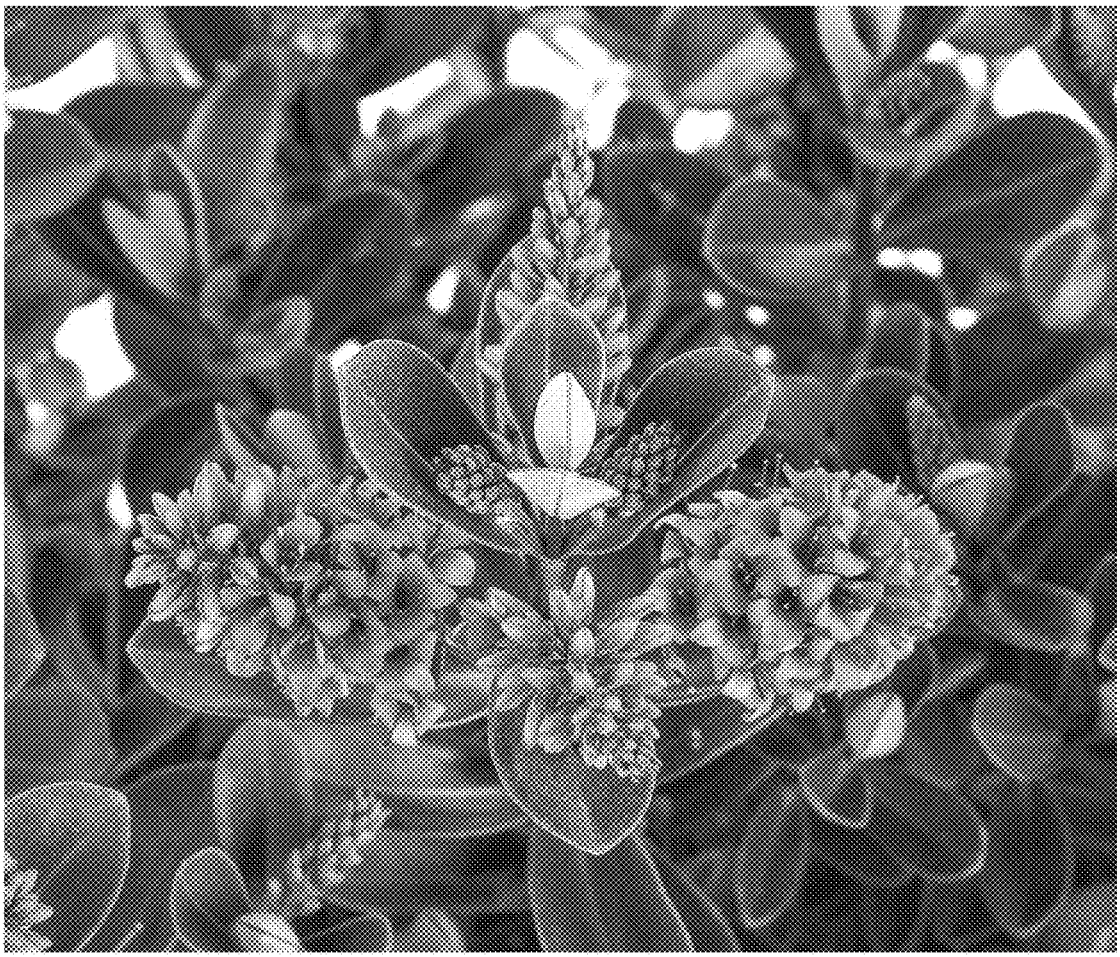

The photograph in FIG. 2 provides a close-up view of the inflorescences and foliage of 'HM1803011'.

The colors in the photographs may differ slightly from the color values cited in the detailed botanical description, which accurately describe the colors of the new *Hebe*.

DETAILED BOTANICAL DESCRIPTION OF THE PLANT

The following is a detailed description of 7-month-old plants of the new cultivar as grown outdoors in 12-cm containers in Wezep, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—An average of 5 weeks from summer into autumn in The Netherlands.

*Plant type.*—Evergreen shrub.

*Plant habit.*—Compact.

*Height and spread.*—Average of 20.3 cm in height (soil level to top of foliar plane), 20.8 cm (soil level to top of floral plane) and 20.5 cm in spread, an average of 70 cm in height and spread in the landscape.

*Cold hardiness.*—At least to U.S.D.A. Zone 8.

*Diseases and pests.*—Low susceptibility to leaf spot disease (*Septoria veronicae*) and downy mildew (*Perenospora* ssp.), no susceptibility or resistance to pests has been observed.

*Root description.*—Fibrous to slightly fleshy.

*Propagation.*—Softwood stem cuttings and tissue culture.

*Root development.*—3 to 4 weeks to initiation roots and 10 weeks to root and bloom as a young plant.

*Growth rate.*—Moderate.

Branch description:

*Branch size.*—Main branches; an average of 7 cm in length and 2 mm in diameter, lateral branches; an average of 11 cm in length and 2 mm in diameter.

*Branch shape.*—Round.

*Branch color.*—Young; 183B, lower side 177B, mature; 148A.

*Branch surface.*—Slightly glossy, moderately to densely covered with very short glandular hairs; 0.1 mm in length, matches surface color.

*Branch strength.*—Strong.

*Internode length.*—Average of 1.2 cm.

*Branching habit.*—Held in an average angle of 35° to vertical, average of 6 primary branches and secondary branches.

Foliage description:

*Leaf shape.*—Narrow obovate to oblanceolate, slightly carinate.

*Leaf division.*—Single.

*Leaf base.*—Cuneate.

*Leaf apex.*—Bluntly acute.

*Leaf venation.*—Pinnate; often with 3 to 5 main veins visible, color; upper surface; 147B to 147C, lower surface; 146C to 146D.

*Leaf margins.*—Entire.

*Leaf attachment.*—Sessile.

*Leaf arrangement.*—Opposite.

*Leaf surface.*—Both surfaces smooth, glabrous and non-rugose, upper surface very slightly glossy, lower surface matte.

*Leaf color.*—Young upper surface; 137B, young lower surface; 146B, mature upper surface; NN137A, base 144C, mature lower surface; 146C.

*Leaf number.*—Average of 12 per lateral branch 11 cm in length.

*Leaf size.*—An average of 3.5 cm in length and 1.15 cm in width.

Flower description:

*Inflorescence type.*—Raceme.

*Inflorescence size.*—Average of 4.1 cm in height and 2.3 cm in width.

*Inflorescence lastingness.*—About 7 days, self-cleaning.

*Flower shape.*—Campanulate.

*Flower fragrance.*—None.

*Flower quantity.*—Average 55 florets per inflorescence, 500 flowers per plant, 3,500 flowers and flower buds per plant.

*Flower arrangement.*—Axillary racemes.

*Flower aspect.*—Outward.

*Flower size.*—Average of 6.5 mm in height, 8 mm in diameter, 1 cm in depth, throat diameter 2 mm, flower tube length 2 mm, flower tube diameter 2.25 mm.

*Peduncles.*—Strong strength, 3.8 cm in length and about 1.5 mm in diameter, 146C in color, held at about a 45° angle to lateral branch, surface is matte and densely covered with very short glandular hairs an average of 0.1 mm in length, matches surface color.

*Pedicels.*—Moderately strong strength, average of 1.5 mm in length and 0.5 mm in diameter, held at about a 45° angle to peduncle, 146C in color, surface is very matte and densely covered with very short glandular hairs; an average of 0.1 mm in length, color matches surface color.

*Flower buds.*—Lanceolate to narrow elliptic, 4 mm in length and 1.5 mm in diameter, color; 63C, immature calyx 138B, surface is matte, smooth and glabrous.

*Calyx.*—Rotate-shaped, average of 2 mm in length and diameter.

*Sepals.*—4, 1 whorl, 1 mm in length, 2 mm in width, ovate in shape, entire margins, arrangement; rotate, acute tip, base cuneate and fused, surfaces glabrous, matte, slightly glossy, color; when opening and fully open upper and lower surface 143C, margins 157A.

*Petals.*—Average 4, 1 whorl, oblong in shape, lower petals moderately reflexed, lower 33% of petals fused, 4 mm in length and 2 mm in width, entire and very slightly concave margins, apex obtuse, upper and lower surface is smooth and glabrous, non-rugose, both surfaces very slightly glossy, color: upper surface when opening; 61C, lower surface when opening; 73B, upper surface when fully open; 64C, lower surface when fully open; 73A and 73B, throat N78C, tube N78C, base N155C.

*Floral bracts.*—A single bract is placed below each individual flower, very short oblong in shape, moderately concave, tip bluntly acute, cuneate base, 2 mm in length, 1 mm in width, both surfaces glabrous and 146C in color.

Reproductive organs:

*Gynoecium.*—Pistil; 1, 9 mm in length, stigma; club-shaped, 5 mm in length, 182B in color, style; 8.5 mm in length and 72B in color, ovary; 138B in color.

*Androecium.*—Stamens; 2, anthers; oblong in shape, 0.75 mm in length, 0.5 mm in width and 177B in color, filaments; 1.25 mm in length, color; 73D, pollen; none observed.

*Fruit and seed.*—None observed to date.

It is claimed:

1. A new and distinct cultivar of *Hebe* plant named 'HM1803011' as herein illustrated and described.

* * * * *